(12) United States Patent
Benson

(10) Patent No.: US 6,972,042 B2
(45) Date of Patent: Dec. 6, 2005

(54) QUICK-RELEASE TUBE CLAMP FOR MODULAR LOWER LIMB PROSTHETIC SYSTEMS AND METHOD THEREOF

(75) Inventor: Richard Myrle Benson, Rifle, CO (US)

(73) Assignee: Ampu-Clamp LLC, Rifle, CO (US)

( * ) Notice: Subject to any disclaimer, the term of this patent is extended or adjusted under 35 U.S.C. 154(b) by 1 day.

(21) Appl. No.: 10/650,647

(22) Filed: Aug. 28, 2003

(65) Prior Publication Data

US 2005/0049720 A1    Mar. 3, 2005

(51) Int. Cl.$^7$ ............................. A61F 2/80; F16B 2/02; F16B 2/14
(52) U.S. Cl. .................. 623/38; 403/DIG. 4; 403/314; 403/374.5
(58) Field of Search .................. 623/38, 27; 403/109.5, 403/DIG. 4, 104, 110, 314, 320, 374.5, 374.1, 403/373

(56) References Cited

U.S. PATENT DOCUMENTS

| | | |
|---|---|---|
| 3,545,009 A | 12/1970 | Colley |
| 3,545,046 A | 12/1970 | Colley |
| 3,659,294 A | 5/1972 | Glabiszewski |
| 4,054,394 A | 10/1977 | Neuman |
| 4,221,007 A * | 9/1980 | Wilson .......................... 623/38 |
| 4,268,922 A | 5/1981 | Marsh et al. |
| 4,299,396 A * | 11/1981 | Becker et al. ............... 277/630 |
| 4,430,017 A * | 2/1984 | Stefancich ................... 403/104 |
| 4,523,338 A * | 6/1985 | May ............................. 623/38 |
| 4,564,365 A * | 1/1986 | Winer et al. .................. 623/27 |
| 4,744,690 A * | 5/1988 | Hsieh .......................... 403/104 |
| 4,938,775 A | 7/1990 | Morgan |
| 5,405,406 A | 4/1995 | Hiemisch |
| 5,443,522 A | 8/1995 | Hiemisch |
| 5,507,837 A | 4/1996 | Laghi |
| 5,556,222 A * | 9/1996 | Chen .......................... 403/323 |
| 5,571,211 A | 11/1996 | Hiemisch et al. |
| 5,653,511 A * | 8/1997 | Herkoperec et al. ..... 301/124.2 |
| 5,755,812 A | 5/1998 | Becker et al. |
| 5,851,194 A | 12/1998 | Fratrick |
| 5,887,835 A * | 3/1999 | Hein et al. ................... 248/161 |
| 5,928,290 A | 7/1999 | Gramnas |
| 5,961,186 A * | 10/1999 | Phillips .................... 301/124.2 |
| 5,976,190 A | 11/1999 | Anhalt et al. |
| RE36,521 E | 1/2000 | Hiemisch |
| 6,051,026 A * | 4/2000 | Biedermann et al. ......... 623/38 |
| 6,093,210 A | 7/2000 | Gramnas |

(Continued)

FOREIGN PATENT DOCUMENTS

GB    155917    12/1920

Primary Examiner—Alvin J. Stewart
(74) Attorney, Agent, or Firm—Dorr, Carson & Birney, P.C.

(57) ABSTRACT

A quick-release tube clamp and method therefor for locking and releasing a prosthetic pylon/foot component from the socket. The quick-release tube clamp includes a tubular portion, an annular socket portion, and a clamp portion. The tubular portion has a formed slot along a longitudinal length of the tubular portion. The tubular portion forms a cylindrical opening with an inner diameter slightly larger than the outer diameter of the tubular pylon. The annular socket at the upper end of the tubular portion attaches to the socket of the modular lower limb prosthetic system. The clamp portion is located near the lower end of the tubular portion and firmly locks the tubular portion around the tubular pylon when the tubular pylon is inserted into the tubular position and provides a releasing position for removal of the tubular pylon.

1 Claim, 4 Drawing Sheets

U.S. PATENT DOCUMENTS

| | | |
|---|---|---|
| 6,235,062 B1 | 5/2001 | Gramnas |
| 6,299,588 B1 | 10/2001 | Fratrick |
| 6,305,869 B1 | 10/2001 | Chen |
| 6,318,741 B1 | 11/2001 | Chen |
| 6,402,789 B1 | 6/2002 | Gramnas |
| 6,416,555 B1 | 7/2002 | Dillenburg et al. |
| 6,458,163 B1 | 10/2002 | Slemker et al. |
| 6,561,124 B1 * | 5/2003 | Marczynski et al. ........ 116/309 |
| 6,581,492 B1 | 6/2003 | Chen |
| 6,601,712 B2 * | 8/2003 | Dean et al. .................... 211/20 |
| 6,689,171 B2 * | 2/2004 | Slemker et al. ................ 623/33 |
| 6,712,376 B2 * | 3/2004 | Eberhardt et al. .......... 280/293 |
| 6,758,380 B1 * | 7/2004 | Kolda ........................ 224/315 |
| 2005/0041966 A1 * | 2/2005 | Johnson ..................... 396/428 |

\* cited by examiner

QUICK-RELEASE TUBE CLAMP FOR MODULAR LOWER LIMB PROSTHETIC SYSTEMS AND METHOD THEREOF

BACKGROUND OF THE INVENTION

1. Field of the Invention

The invention relates to a mechanism for releasing a prosthetic pylon/foot component from a lower limb prosthetic socket and, more particularly, to providing a quick-release for such a mechanism and method therefor.

2. Discussion of the Background

With the introduction of modular prosthetics in the mid-1990's, a number of conventional mechanisms have been designed to connect and to release a prosthetic pylon/foot component from the prosthetic socket of a user. In the lower limb prosthesis industry, a conventional link-plate is rigidly attached to the base of the socket, the link-plate typically has a downwardly extending pyramidal boss. A connector with an annular socket usually having four set screws couples to the pyramidal boss. The four set screws are adjusted and tightened, usually by a trained professional, to provide proper fitting for the prosthetic pylon/foot component. This is found, for example, in U.S. Pat. Nos. 3,659,294 and 6,458,163.

One prior approach for coupling to the pyramidal boss of the link-plate is set forth in U.S. Pat. No. 5,571,211 which provides a tubular adapter. The tubular adapter has the annular socket with four set screws for coupling to the pyramidal boss, a connecting sleeve with a formed axial slot between two outer tabs, and a plastic clamping cuff placed in an annular groove of the sleeve. When the tubular pylon of the prosthetic pylon/foot component is inserted in the sleeve, a clamping bolt engaging the two outer tabs is tightened to cause the plastic clamp to press against the inserted tubular pylon. The clamping bolt, outer tabs and plastic clamp provide a release mechanism requiring a separate tool for tightening and releasing. The tool is carried by the user.

A continuing need exists to improve such release mechanisms. For example, the simple act of putting on and taking off pants underscores the need for a lower limb prosthetic system wherein the pylon/foot component can be quickly removed so that the pants can be pulled over the socket and then reattaching the pylon/foot component to the socket through the leg of the pants. For active persons, a further need exists to quickly remove the prosthetic pylon/foot component to either attach a new prosthetic pylon/foot component (for the desired activity) or to adjust the present prosthetic pylon/foot component (such as for toe-in or toe-out). For example, users may require different pylon/foot components based on the activity, such as different feet with different shoes, wet-legs, running legs, climbing legs, riding legs, etc. By way of further example, when a user continually walks or walks uphill, the residual limb may tire from being at the same angle and/or pressure. The toe-in and toe-out can be adjusted to change the angle and/or pressure. Many other situations present themselves where releasing and removing/adjusting the pylon/foot component is advantageous to a user: sitting for extended periods of time, riding in a car, crawling, taking a shower, etc.

In situations where the pylon/foot component is frequently removed, a further need exists to provide a release mechanism that is durable. For example, in a situation where a prosthetic lower limb is reattached to the socket and a plastic part strips or fails, the user may be in a situation (such as out of doors, at a mall, etc.) where a replacement part is not available and the prosthetic lower limb is unable to be reattached. This presents a substantial inconvenience to the user. Some users also carry replacement parts with them in the event a failure occurs. A further need exists to provide an attachment mechanism which does not require the use of a special tool that would have to be also carried with the user.

The, following patents provide release mechanisms not requiring a separate tool.

U.S. Pat. No. 4,564,365 discloses a quick change mechanism for a limb prosthesis requiring the use of two opposing cam latches located on opposite sides of a tubular member that allows the pylon/foot component to be released from the socket portion. This occurs by moving convex arches into and out of a recessed cylindrical area. A fail safe retainer clip engages the ends of the cam latches to prevent accidental release.

U.S. Pat. No. 4,938,775 recognized that the above '365 patent provided a complex design that was not strong enough for athletic activities and would require substantial modification for use with existing artificial legs. The '775 patent provides a first attaching member permanently attached to the lower end of the socket to releasably retain a second member on the removable support prosthesis. A handle is moved to engage and clamp the two mating members together. When the handle is raised, the attaching members release and the prosthesis can be removed. The '775 patent requires each different prosthetic pylon/foot component to have an attaching plate and a bearing attached to the upper end of the pylon. In use, the user must align and then seat the two attaching members together.

U.S. Pat. Nos. 5,928,290; 6,093,210; 6,235,062; and 6,402,789 provide a fastening device for a prosthesis to permit withdrawal of the cylindrical insert into an inclined washer fastening device.

British patent provisional specification No. 155,917 utilizes a sliding sleeve to lock a steel ball in a groove so that a prosthesis can be removed without use of tools.

In an entirely different technological area, quick-release mechanisms are conventionally used. For example, for bicycle seats, U.S. Pat. Nos. 6,581,492; 6,305,869; and 6,318,741 all relate to quick-release mechanisms. In another example for rotary die cutting, U.S. Pat. No. 4,054,394 discloses a curved lever arm shaped to conform to the contour of the circular head along with a spring clip to hold the lever in place to prevent accidental release.

A continuing need exists for a quick-release mechanism and method therefor for locking and releasing a prosthetic pylon/foot component from the socket without the use of a special tool. A further need exists for a quick-release mechanism which is simply constructed with few parts and which is durable for an active user. A need exists for a quick-release mechanism that does not require any alignment and seating of the locking mechanism, does not rotate when locked, and that does not require modification of the conventional prosthesis pylon of the pylon/foot component.

SUMMARY OF THE INVENTION

The present invention solves the afore-said needs by providing a quick-release mechanism and method therefor for locking and releasing a prosthetic pylon/foot component from the socket without the use of a special tool. The present invention further provides a quick-release mechanism constructed of only a few parts, all of which are durable for an active user. The present invention provides a quick-release mechanism that does not require any alignment in seating of the locking mechanism, does not rotate when in the locking position, and does not require modification of conventional pylon/foot components.

The quick-release tube clamp of the present invention includes a tubular portion, an annular socket portion, and a clamp portion.

The tubular portion has at least one formed slot along a longitudinal length of the tubular portion, and the tubular portion forms a cylindrical opening with an inner diameter slightly larger than the outer diameter of the tubular pylon.

The annular socket at the upper end of the tubular portion attaches to the socket of the modular lower limb prosthetic system.

The clamp portion is located near the lower end of the tubular portion firmly locks the tubular portion around the tubular pylon when the tubular pylon is inserted into the tubular position and provides a releasing position for removal of the tubular pylon. The clamp portion includes a pair of opposing tabs located on opposing sides of the formed slot and a handle. The handle has a cam at one end and is curved to follow the shape of the tubular portion. When the handle is moved into the locking position, the cam operates on the pair of opposing tabs to lock the tubular portion around the inserted tubular pylon by reducing the width of the formed slot.

DETAILED DESCRIPTION OF THE INVENTION

Figure 1:
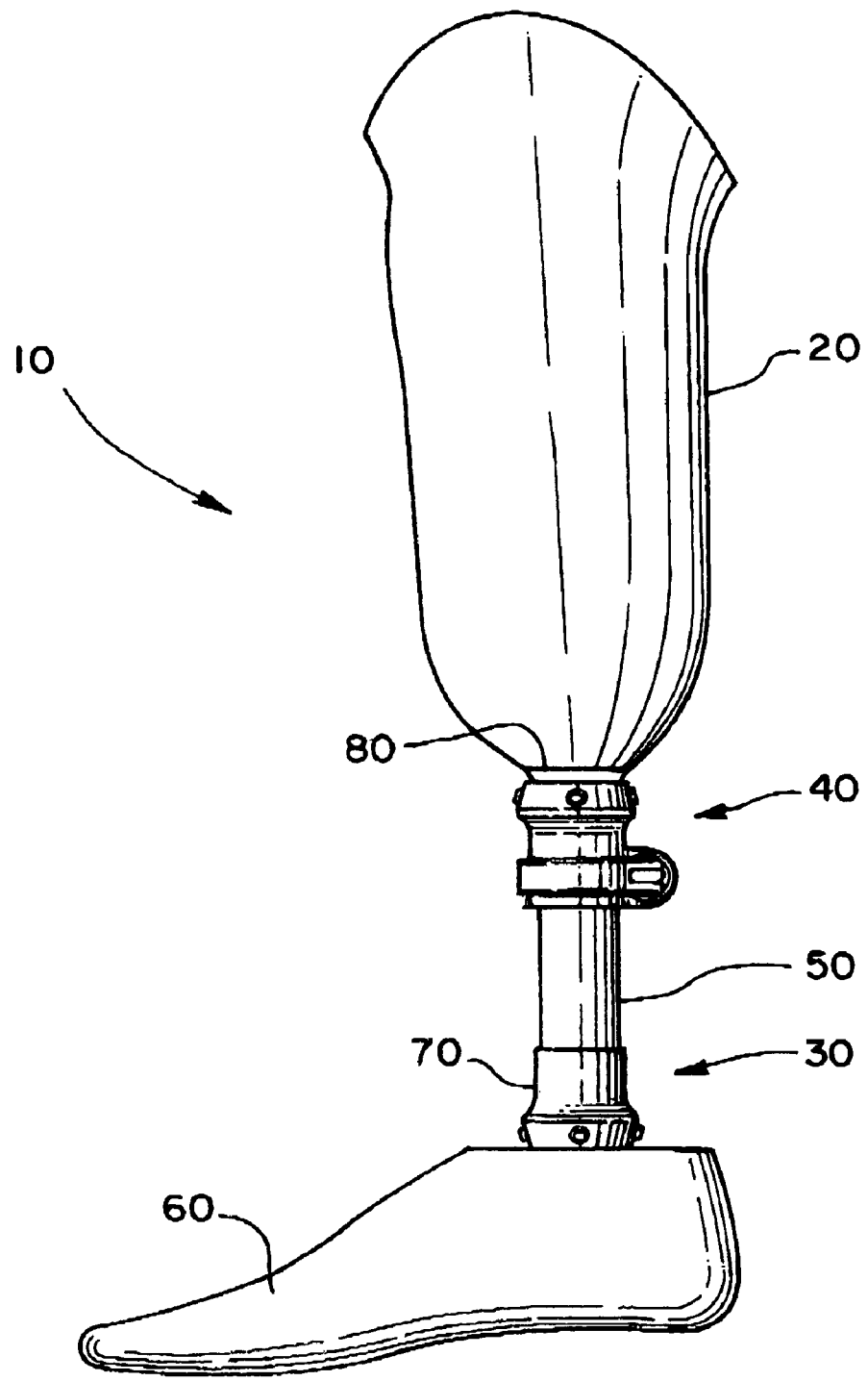
FIG. 1 sets forth a side view of the modular lower limb prosthetic system of the present invention.

In FIG. 1, a modular lower limb prosthetic system 10 is shown to include a conventional socket 20 and a conventional pylon/foot component 30. The quick-release tube clamp 40 of the present invention is shown firmly connecting the pylon/foot component 30 to the socket 20.

Figure 2:
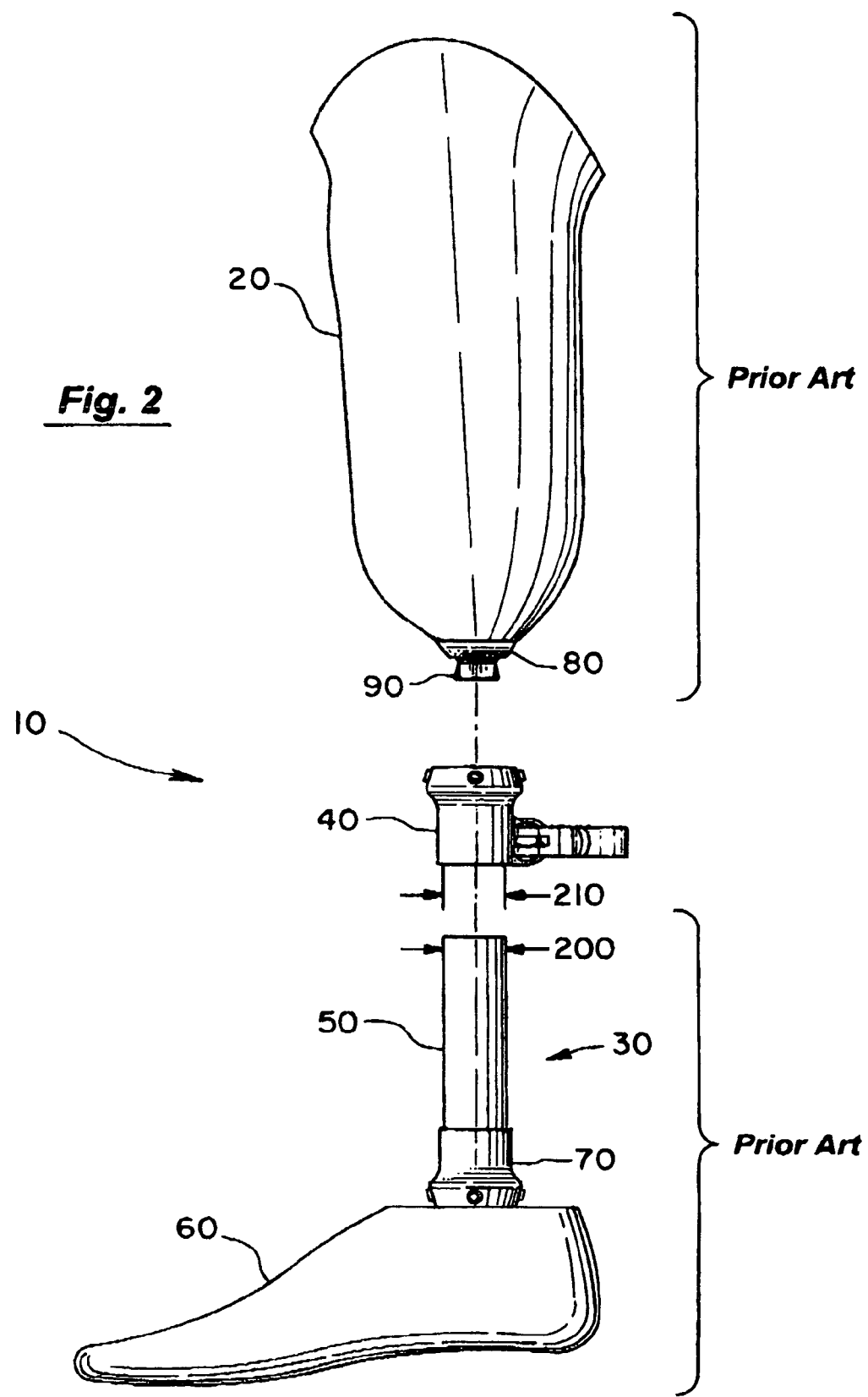
FIG. 2 sets forth the modular lower limb prosthetic system of FIG. 1 showing the prior art socket and the prior art pylon/foot component, as well as the quick-release tube clamp of the present invention taken apart.

In FIG. 2, the quick-release tube clamp 40 of the present invention is shown released from the socket 20 and released from the pylon/foot component 30. The conventional pylon/foot component 30 also has a conventional tubular pylon 50 and a conventional prosthetic foot 60. The tubular pylon 50 is connected with a conventional connector 70 to the prosthetic foot 60. It is to be expressly understood that the pylon/foot component 30 is conventional, as is the tubular pylon 50, the prosthetic foot 60, and the connector 70. Connector 70 can be a complex connector or simply using epoxy to glue the tubular pylon 50 to the foot 60. The present invention is not limited to the pylon/foot component 30 and any of a number of different such components 30 could be utilized with the quick-release tube clamp 40 of the present invention. The fact that the pylon/foot component 30 is conventional is also shown as "prior art" in FIG. 2.

Likewise, socket 20 is conventional as is the link-plate 80 having a downwardly extending pyramidal boss 90. The fact that the socket 20, link-plate 80, and pyramidal boss 90 are conventional is shown in FIG. 2 as "prior art."

Figure 3:
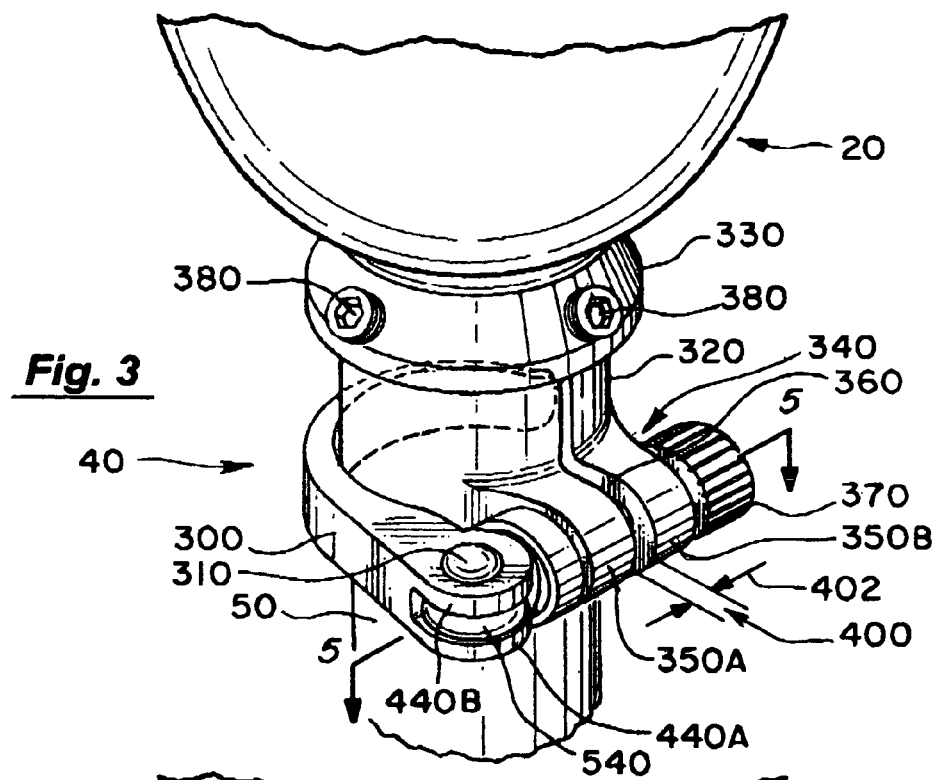
FIG. 3 sets forth a perspective view of the quick-release tube clamp of the present invention in a locked position.
Figure 4:
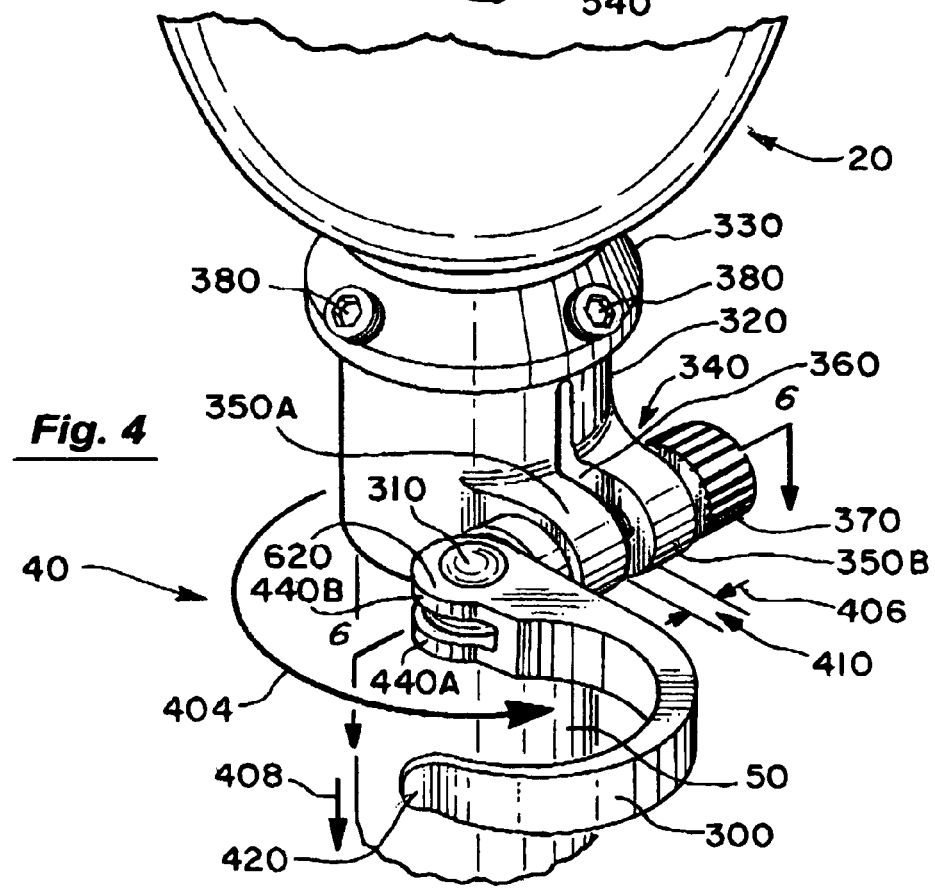
FIG. 4 is a perspective view of the quick-release tube clamp of the present invention in the unlocked or released position.

In FIGS. 3 and 4, the quick-release tube clamp 40 of the present invention is shown locked in place (FIG. 3) and released (FIG. 4). The quick-release tube clamp 40 has a handle 300 which pivots about a pivot pin 310. The quick-release tube clamp 40 also has a tube portion 320 and an annular socket portion 330. The handle 300 engages a clamp portion 340 of the quick-release tube clamp 40. In one embodiment, the portions 320, 330 and 340 are integral. In other embodiments, the portions 320, 330 and/or 340 may constitute separate structures. The clamp portion 340 also includes two raised opposing tabs 350A and 350B. A slot 360 is formed in the tubular portion 320 and between the opposing tabs 350A and 350B of the clamp portion 340. The clamping portion 340 also has a knurled thumb nut 370.

The annular socket portion 330 has four set screws disposed there around which are used to connect to the pyramidal boss 90 on the link-plate 80 affixed to the socket 20. Again, it is to be expressly understood that the use of the four set screws 380 and the provision of the annular socket 330 as it interconnects to the pyramidal boss 90 is conventional. A trained professional will adjust the set screws 380 to provide a proper fit to the user of the modular lower limb prosthetic pylon/foot component 10. It is to be expressly understood that the teachings of the present invention are not limited to the use of four set screws or the shape of the annular socket portion 330 and that any suitable number of set screws 380, shape of the annular socket 330 could be utilized under the present invention.

In operation, the user of the quick-release tube clamp 40 of the present invention uses thumb nut 370 for setting how tight the quick-release tube clamp 40 should engage the tubular pylon 50. The user of the quick-release tube clamp 40 inserts and locks (FIG. 1) or releases (FIG. 2) the tubular pylon 50 of the pylon/foot component 30 from the quick-release tube clamp 40 of the present invention.

As shown in FIG. 3, the handle 300 is in a locked position around the tubular portion 320 so that a narrower distance of 400 is achieved between opposing tabs 350A and 350B as shown by arrows 402. When the handle 300 is released in the direction of arrow 404, as shown in FIG. 4, a distance of 410 between the opposing tabs 350A and 350B is obtained as shown by arrows 406. The formed slot 360 acts mechanically as a spring. The handle 300 moving into the locked position (FIG. 5) uses the cam 620 to act against the spring and narrow the width of the slot 360 to 400. When the handle is moved into the release position (FIG. 6), the cam 620 releases and the slot 360 returns to its release width 410. It is to be expressly understood that the distances 400 and 410 are shown illustrated to be wider than found in actual use so that the teachings of the present invention can be appreciated. It is to be expressly understood that the distance 400 can be quite minimal including with the opposing tabs 350A and 350B actually touching or abutting each other. The formed slot is a desired longitudinal length in the tubular portion and is open at the lower end as shown.

It is appreciated that the quick-release tube clamp 40 of the present invention enables the user to simply move the handle 300 in the direction of arrow 404 to release the tubular pylon 50. Only one movement is required for release. When the quick-release tube clamp 40 of the present invention is locked in position as shown in FIG. 3, the user simply takes a finger and grips outwardly raised portion 420 of the handle 300 to move the handle 300 in the direction of arrow 404. In one movement of the handle 300 to the fully opened position as shown in FIG. 4, the user of the present invention can quickly remove the pylon foot 50 in the direction of arrow 408 (FIG. 4) from the quick-release tube clamp 40 of the present invention.

As shown in FIGS. 3 and 4, the clamping portion 340 is located at the lower end of the tubular portion 320 and the annular socket 330 is located at the upper end. The terms "upper end" and "lower end" are relative to the direction shown in FIGS. 1 and 2 with respect to the socket 20 and the foot 60, respectively. The annular socket portion 330 is at the upper end of the tube clamp 40 and the clamping portion 340, in one embodiment, is at the lower end of the tube clamp 40. In another embodiment, the clamping portion 340 is offset from the lower end so that the tubular portion 320 may extend downwardly from the clamping portion 340. Use of the term "near the lower end" of the tube clamp 40 shall mean at or offset above the lower end of the tube clamp 40.

Figure 5:
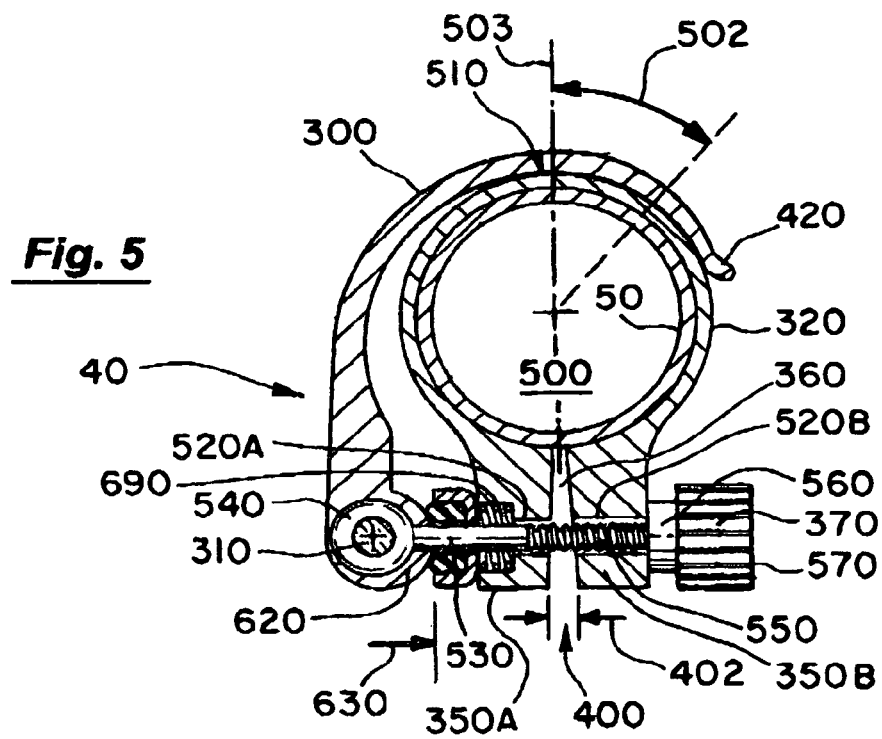
FIG. 5 is a cross-sectional view along lines 5—5 of FIG. 3.
Figure 6:
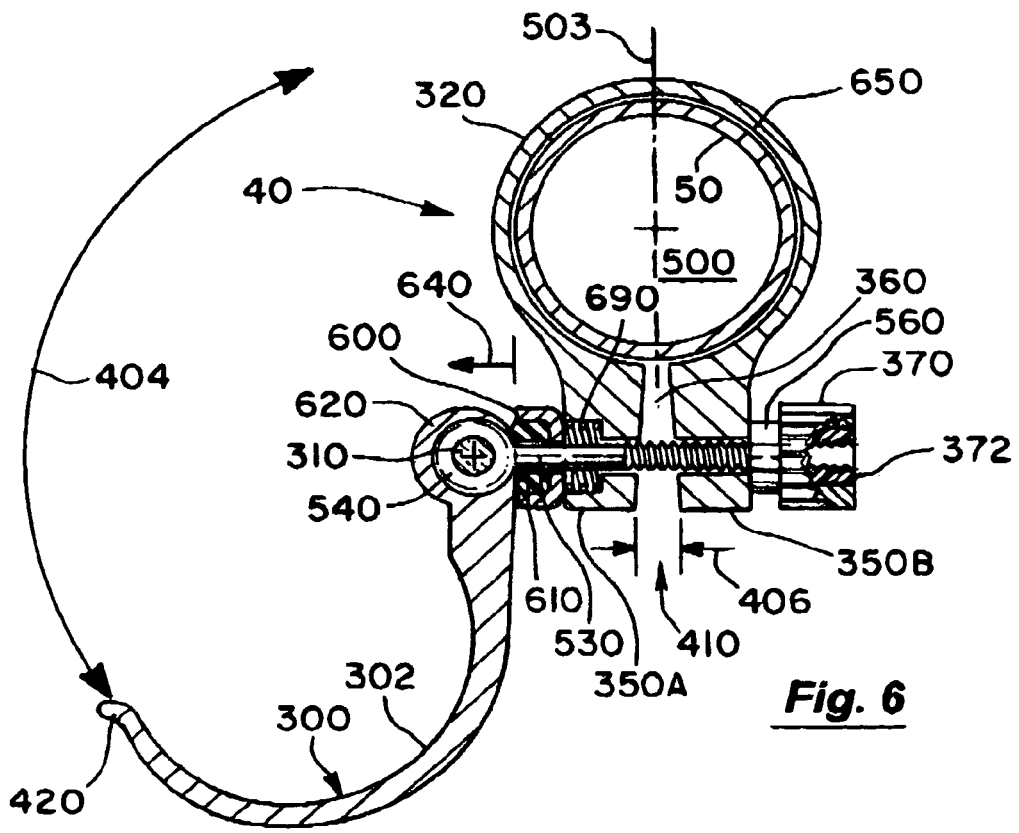
FIG. 6 is a cross-sectional view along lines 6—6 of FIG. 4.

In FIGS. 5 and 6, cross-sectional views of the quick-release tube clamp 40 of the present invention are shown corresponding to the locked position shown in FIG. 3 and to the released position shown in FIG. 4, respectively. The tube clamp 40 has a formed cylindrical opening 500 having an inside diameter 210 slightly greater than the outside diameter 200 (FIG. 2). It is to be understood that the outside configuration of the tubular portion 320 in one embodiment is cylindrical, but that any suitable configuration could be utilized such as, for example, multi-sided, partially cylindrical and partially multi-sided, etc.

In FIGS. 5 and 6, the quick-release tube clamp 40 of the present invention is shown in greater detail. In FIG. 5, the handle 300 in the locked position terminates in slightly raised end 420. As shown in FIG. 5, raised end 420 is raised from the tubular portion 320 to enable the finger of the user to grip end 420 and to lift and move the handle 300 in the direction of arrow 404. However, in the locked position as shown in FIG. 5, the handle 300 is, in one embodiment, long enough to extend over 45° from the diameter 503 of the tubular portion 320 through the formed slot 360 (as shown by arrow 502). In this embodiment (i.e., distance 502 is greater than 45%), if anything catches on the raised end 420, accidental release is less likely to happen as the handle 300 is more tightly coupled to the tubular body 320. This is one embodiment of the present invention. In this embodiment, the handle 300 is curved to abut the curved surface of the tubular portion 320 in the region shown as 510, at least including the area shown by arrow 502. In other embodiments where the tubular portion 320 is multi-sided, the interior side 302 of the handle 300 can have a mating multi-sided surface. This abutment region 510 provides an area of firm engagement of the handle 300 with the tubular portion 320. Raised end 420 is designed to be minimal so as to prevent it from catching on something, yet convenient for a user to grip with a finger so that accidental release of the handle 300 from the tubular body 320 in the direction of arrow 404 does not occur. In other embodiments of the quick-release tube clamp 40 of the present invention, the handle 300 can be of any desirable length. In other embodiments of the present invention, the raised end 420 may take on different shapes and configurations. In other embodiments of the present invention, a separate latching mechanism, not shown, could be utilized to engage the handle 300 so as to further lock the handle 300 to the tubular body 320 so as to prevent accidental release.

In FIGS. 5 and 6, the opposing tabs 350A and 350B have formed holes 520A and 520B for receipt of a bolt 530. One end of the bolt 530 has a loop 540 for receiving the pin 310 and the other end of the bolt 530 is threaded 550 and threadly engages the thumb nut 370. The thumb nut 370 has a portion 560 that sets the thumb nut knurled portion 570 slightly away from opposing tab 350B. The thumb nut 560, in one embodiment, has an internal nylon insert 372 that engages the threads 550 of the bolt 530 so as to prevent the thumb nut 370 from loosening on its own after being adjusted by the user to a desired tightness. In other embodiments of the present invention, the thumb nut 370 could engage a lock washer, not shown, to accomplish the same task. Other embodiments of the thumb nut 570 include any mechanism that allows selective adjustment by the user of the thumb nut 370 for desired tightness of the quick-release to clamp 40 of the present invention against the tubular pylon 50 and to maintain the desired tightness.

Also shown in FIGS. 5 and 6, in one embodiment, is a camming cup 600 having a camming nylon insert 610. The insert 610 provides a "low wear" point for the cam 620 to operate on. In other embodiments of the present invention, such a nylon insert is not used. The handle 300 at the end connected to the pin 310 has a cam surface 620. In FIG. 5, when the handle 300 is locked, the cam surface 620 forcibly abuts against the nylon insert 610 in the camming cup 600 to move tabs 350A and 350B together to obtain distance 400 when the handle is locked as shown in FIG. 5. This is shown by arrow 630 in FIG. 5. When the handle 300 is fully released, the camming surface 620 is removed and the lock is in the fully released position as shown by arrow 640. The camming surface 620 is found on each of the opposing ends 440A and 440B of the handle 300. The loop 540 is disposed between opposing ends 440A and 440B. The tension spring 690 is designed to hold the camming cup 600 in place against the handle 300. In other embodiments of the present invention, the tension spring 690 is not used. In other embodiments of the present invention, the camming cup 600 is not used.

As shown in FIG. 6, in the fully released position, a space 650 now exists between the outer surface of the tubular pylon 50 and the inner surface of the tubular clamp portion 320 so that the user can easily remove the pylon/foot component 30 from the quick-release tube clamp 40 of the present invention in the direction of arrow 408 (FIG. 4).

In FIGS. 3 through 6, one embodiment of the quick-release tube clamp 40 of the present invention has been shown. In other embodiments, the opposing tabs 350A and 350B can be designed closer to the tubular body 320 embodying more curved surfaces so as not to jut out as far (as shown in these figures) from the tubular body portion 320. The quick-release tube clamp 40 of the present invention is not limited to the precise mechanical design shown in FIGS. 3 through 6. Any other mechanical embodiment for moving opposing tabs 350A and 350B together under action from a single lever moving in the direction of arrow 404 could be utilized under the teachings of the present invention.

Under the method of the present invention, and with reference to FIG. 2, the tube clamp 40 of the present invention is in the released position as shown in FIGS. 2, 4 and 6. The user inserts the tubular pylon 50 into the tubular portion 320 as shown in FIG. 6. At this point in the method, the inside diameter of the tubular portion is slightly greater than the outside diameter of the pylon 50 to leave a space 650. The user positions the foot 60 for proper toe-in/toe-out. The user then moves the handle 300 in a direction of arrow 404 to lock the tubular portion 320 about the pylon 50 as fully described above. The locking position is shown in FIGS. 1, 3 and 5. The above method operates in reverse to release the pylon 50 from the tube clamp 40 of the present invention.

The above disclosure sets forth a number of embodiments of the present invention. Those skilled in this art will however appreciate that other arrangements or embodiments, not precisely set forth, could be practiced under the teachings of the present invention.

I claim:

1. A modular lower limb prosthetic system comprising:
   a pylon/foot component, said pylon/foot component having a tubular pylon with an outer diameter,
   a socket having a pyramidal boss,
   a quick-release tube clamp, the quick release tube clamp comprising:
   (a) a tubular portion having an outer diameter, an upper end, and a lower end, said tubular portion having at least one formed slot along a longitudinal length of said tubular portion, said tubular portion having a formed cylindrical opening with an inner diameter slightly larger than said outer diameter of said tubular pylon,
   (b) an annular socket portion, integral on said tubular portion, at the upper end of the tubular portion for attaching to the pyramidal boss of said socket,
   (c) a plurality of screws engaging said annular socket portion, said plurality of adjusting screws securely connecting said annular socket to said pyramidal boss of said socket,
   (d) a clamp portion near the lower end of said tubular portion, said clamp portion locking said tubular portion around said tubular pylon in a locking position when said tubular pylon is inserted into said tubular portion, said clamp portion releasing said tubular portion from said tubular pylon in an unlocked position, said clamp portion comprising:

(i) a pair of opposing tabs, integral on said tubular portion, located on opposite sides of said formed slot,
   (ii) a handle connected to said pair of opposing tabs, said handle having a formed cam at one end, said formed cam operative in said locking position on said pair of opposing tabs for holding said pair of opposing tabs in said locking position by reducing the width of said formed slot, said formed cam operative in said unlocking position for releasing said pair of opposing tabs for rotation of said pylon/foot component with respect to said socket in said modular lower limb prosthetic system so as to provide toe-in and toe-out adjustment,
   (iii) a bolt,
   (iv) a thumb nut interconnected to said bolt, said bolt operatively connected to said handle, said thumb nut abutting one of said pair of opposing tabs to provide adjustment to the width of said formed slot when said handle is operated in said locking position, said thumb nut having an internal threaded insert for securing said thumb nut to said bolt after adjustment,
   (v) a camming cup disposed between one of said pair of opposing tabs and said cam,
   (vi) a tension spring between the aforesaid one of said opposing tabs and said camming cup to hold said camming cup against said cam,
   (vii) a nylon insert in said camming cup to provide a low wear point when said cam abuts against said camming cup to operate said quick-release tube clamp into said locking position.

* * * * *